United States Patent
Min

(10) Patent No.: US 10,016,607 B2
(45) Date of Patent: Jul. 10, 2018

(54) SYSTEMS AND METHODS FOR TRACKING STROKE VOLUME USING HYBRID IMPEDANCE CONFIGURATIONS EMPLOYING A MULTI-POLE IMPLANTABLE CARDIAC LEAD

(75) Inventor: Xiaoyi Min, Thousand Oaks, CA (US)

(73) Assignee: PACESETTER, INC., Sylmar, CA (US)

( * ) Notice: Subject to any disclaimer, the term of this patent is extended or adjusted under 35 U.S.C. 154(b) by 1937 days.

(21) Appl. No.: 13/023,408

(22) Filed: Feb. 8, 2011

(65) Prior Publication Data

US 2012/0203090 A1 Aug. 9, 2012

(51) Int. Cl.
| | | |
|---|---|---|
| A61N 1/365 | (2006.01) | |
| A61B 5/029 | (2006.01) | |
| A61B 5/053 | (2006.01) | |
| A61B 5/0295 | (2006.01) | |
| A61B 5/00 | (2006.01) | |
| A61B 5/042 | (2006.01) | |
| A61N 1/362 | (2006.01) | |

(52) U.S. Cl.
CPC .......... *A61N 1/36521* (2013.01); *A61B 5/029* (2013.01); *A61B 5/0295* (2013.01); *A61B 5/0535* (2013.01); *A61B 5/0538* (2013.01); *A61B 5/0031* (2013.01); *A61B 5/0422* (2013.01); *A61B 5/686* (2013.01); *A61B 5/6869* (2013.01); *A61N 1/3627* (2013.01)

(58) Field of Classification Search
USPC ............................................ 600/547; 607/28
See application file for complete search history.

(56) References Cited

U.S. PATENT DOCUMENTS

| 6,522,923 | B1 | 2/2003 | Turcott | |
|---|---|---|---|---|
| 7,447,543 | B2 * | 11/2008 | Belalcazar et al. | ........... 600/547 |
| 2005/0090870 | A1 | 4/2005 | Hine et al. | |

(Continued)

FOREIGN PATENT DOCUMENTS

WO 2005039690 5/2005

OTHER PUBLICATIONS

Webster, J. "Medical Instrumentation: Application and Design" John Wiley and Sons Inc, Hoboken, NJ. 1998. pp. 359-371.*

(Continued)

*Primary Examiner* — Luther G Behringer

(57) ABSTRACT

Techniques are provided for use with an implantable medical device for assessing stroke volume or related cardiac function parameters such as cardiac output based on impedance signals obtained using hybrid impedance configurations that exploit a multi-pole cardiac pacing/sensing lead implanted near the left ventricle. In one example, current is injected between a large and stable reference electrode and a ring electrode in the RV. The reference electrode may be, e.g., a coil electrode implanted within the superior vena cava (SVC). Impedance values are measured along a set of different sensing vectors between the reference electrode and each of the electrodes of the multi-pole LV lead. Stroke volume is then estimated and tracked within the patient using the impedance values. In this manner, a hybrid impedance detection configuration is exploited whereby one vector is used to inject current and other vectors are used to measure impedance.

20 Claims, 14 Drawing Sheets

(56) References Cited

U.S. PATENT DOCUMENTS

2006/0271119 A1* 11/2006 Ni ........................ A61N 1/3627
607/9
2009/0157136 A1    6/2009 Yang et al.
2009/0240298 A1*  9/2009 Lian et al. ........................ 607/9

OTHER PUBLICATIONS

M. Lippert et al.; Intracardiac Impedance as a Method for Ventricular Volume Monitoring—Investigation by a Finite-Element Model and Clinical Data, 2010.
Mario Bocchiardo et al.; Intracardiac Impedance Monitors Stroke Volume in Resynchronization Therapy Patients, May 2010.
Carsten Stahl, M.D., et al.; Intracardiac Impedance Monitors Hemodynamic Deterioration in a Chronic Heart Failure Pig Model, Sep. 2007.

* cited by examiner

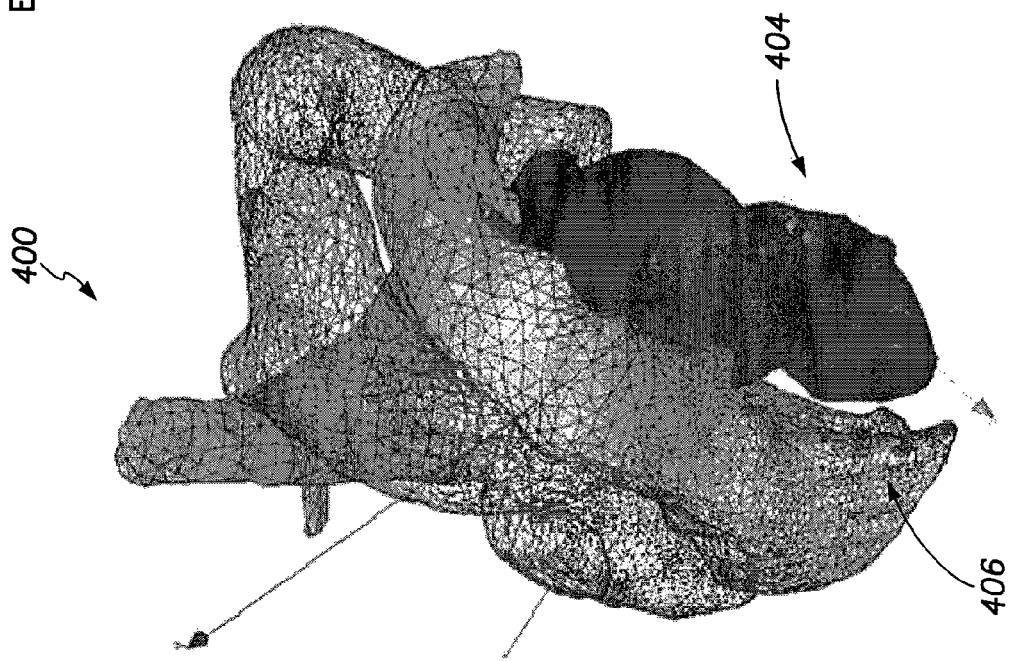
FIG. 9

CURRENT INJECTED RV RING TO SVC COIL WITH
VOLTAGE MEASURED USING LV ELECTRODES — 414

|  | END SYSTOLIC | END DIASTOLIC | DIFF(V)/(%) |
|---|---|---|---|
| INDUCED VOLTAGE AT |  |  |  |
| LV DISTAL (V) | 11.88 | 12.59 | 0.71/6% |
| LV PROXIMAL (V) | 11.22 | 12.06 | 0.84/7% |
| TOTAL P (W) | 24.16 | 26.14 | 8% |
| R (ohms) | 103.5 | 95.6 | 8% |
| I (A) | 0.48 | 0.52 | 8% |
| LV disR (ohms) | 22.7 | 24.1 | 1.387/5.3% |
| LV proxR (Ohms) | 21.5 | 23.1 | 1.607/6.2% |
| SUM OF SLV | 44.19 | 47.15 | 2.96/(6%) |

416　418　420

CURRENT INJECTED RV RING TO CAN WITH
VOLTAGE MEASURED USING LV ELECTRODES

|  | END SYSTOLIC | END DIASTOLIC | DIFF(V)/(%) |
|---|---|---|---|
| INDUCED VOLTAGE AT |  |  |  |
| LV DISTAL (V) | 18.0 | 18.79 | 0.79/4% |
| LV PROXIMAL (V) | 17.62 | 18.43 | 0.81/4% |
| TOTAL P (W) | 20.3 | 21.85 | 7.1% |
| R (ohms) | 123.3. | 114.4 | 7.1% |
| I (A) | 0.406 | 0.437 | 7.6% |
| LV disR (ohms) | 44.3 | 46.3 | 1.9/4% |
| LV proxR (Ohms) | 43.4 | 45.4 | 2.0/4% |
| SUM OF Δ ZLV | 87.8 | 91.7 | 309/4% |

SYSTEMS AND METHODS FOR TRACKING STROKE VOLUME USING HYBRID IMPEDANCE CONFIGURATIONS EMPLOYING A MULTI-POLE IMPLANTABLE CARDIAC LEAD

FIELD OF THE INVENTION

The invention generally relates to implantable cardiac rhythm management devices such as pacemakers and implantable cardioverter-defibrillators (ICDs) and cardiac resynchronization therapy (CRT) devices and, in particular, to techniques for assessing stroke volume using implantable devices equipped with multi-pole leads and further to techniques for optimizing pacing delays based on stroke volume and for detecting and tracking heart failure.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

In view of the potential severity of heart failure, it is highly desirable to detect its onset within a patient and to track its progression so that appropriate therapy can be provided. Many patients suffering heart failure already have pacemakers or ICDs implanted therein or are candidates for such devices. Accordingly, it is desirable to provide such devices with the capability to automatically detect and track heart failure. Physiological parameters that can be used to aid in the detection and tracking of heart failure include stroke volume and related cardiac function parameters. Cardiac function is a measure of the overall effectiveness of the cardiac system of a patient and is typically represented in terms of, one or more of, stoke volume, cardiac output, end-diastolic volume, end-systolic volume, ejection fraction or cardiac output index. Stroke volume is the amount of blood ejected from the left ventricle during systole. Cardiac output is the volume of blood pumped by the left ventricle per minute (or stroke volume times the heart rate). End-diastolic volume (EDV) is the volume of blood in the chamber at the end of the diastolic phase, when the chamber is at its fullest. End-systolic volume (ESV) is the volume of blood in the chamber at the end of the systolic phase, when the chamber contains the least volume. Ejection fraction (EF) is percentage of the EDV ejected by the ventricle per beat. Cardiac index is the volume of blood ejected per minute normalized to the body surface area of the patient. Other factors representative of cardiac function include the contractility of the left ventricle or the maximum rate of change of pressure with time (i.e. max dP/dt).

One promising technique for estimating at least some of these physiological parameters is to exploit intra-cardiac impedance detected using leads of the implantable device. Publications by Stahl et al. (Stahl et al., "Assessing Acute Ventricular Volume Changes by Intracardiac Impedance in a Chronic Heart Failure Animal Model", PACE Vol. 32, 1395-1401, November 2009 and Stahl et al., "Intracardiac Impedance Monitors Hemodynamic Deterioration in a Chronic Heart Failure Pig Model", Journal of Cardiovascular Electrophysiology, Volume 18, Issue 9, pages 985-990, September 2007) and Bocchiardo et al., "Intracardiac impedance monitors stroke volume in resynchronization therapy patients", Europace (2010) [doi: 10.1093/europace/euq045] reported that intra-cardiac impedance correlates well with stroke volume (r=0.88, 0.82) or EDP (r=0.82 or 0.81) in animals and in patients. However, the impedance range differed widely among individuals. Modeling by Lippert et al., "Intracardiac Impedance as a Method for Ventricular Volume Monitoring—Investigation by a Finite-Element Model and Clinical Data, 2010 J. Phys.: Conf. Ser. 224 012095, showed the range of intra-cardiac impedance can also be very sensitive to left ventricular (LV) lead positions. This would make the estimation of "absolute values" of stroke volume or cardiac output difficult, i.e., values scaled to the proper units. Yet, many clinicians prefer stroke volume or cardiac output since those parameters provide a direct clinical measure that can be helpful in diagnosing conditions and guiding treatment.

Accordingly, it would be highly desirable to provide improved techniques for estimating stroke volume or cardiac output from impedance signals detected within a patient for informing the clinician, detecting and tracking heart failure or for other purposes such as automatically optimizing pacing delays. It is to these ends that various aspects of the invention are directed.

SUMMARY OF THE INVENTION

In an exemplary embodiment, a method is provided for use with an implantable medical device for implant within a patient having a lead system including a right ventricular (RV) lead and a multi-pole left ventricular (LV) lead implanted via the coronary sinus (CS). Current is injected between a reference electrode and an electrode in the RV. The reference electrode is preferably a relatively large and stable electrode (i.e., one that is relatively insensitive to patient motion artifacts and tissue property changes) such as a coil electrode implanted within the superior vena cava (SVC) of the patient. Impedance values are measured along a set of different sensing vectors between the stable reference electrode and each of the electrodes of the multi-pole LV lead. Then, a parameter representative of stroke volume is estimated and tracked within the patient from a selected combination of the impedance values. In this manner, a hybrid impedance detection configuration is exploited whereby one vector is used to inject current and other vectors are used to measure impedance.

In an illustrative example, the implantable device is a pacemaker, ICD or CRT device having an RV lead with a pair of tip and ring electrodes and a quad-pole LV lead implanted via the CS with a distal tip electrode (D1), a proximal ring electrode (P4), and a pair of intermediate ring electrodes (M2 and M3). For convenience, the LV electrodes are identified by the index "i" where i=1 refers to the D1 electrode, i=2 refers to the M2 electrode, i=3 refers to the M3 electrode and i=4 refers to the P4 electrode. The RV lead also has an SVC coil electrode, which is used as the reference electrode. Current is injected using the RV ring and the SVC coil. As such, the current injection vector exploits the relatively large and stable SVC coil, which generates a relatively wide electrical field for impedance measurement purposes. In particular, the injection vector can create spherical iso-potential surfaces around the RV ring enabling the LV electrodes to sense movement of the heart affected by LV contraction and stroke volume. Note that the relatively wide field encompasses at least some non-cardiac thoracic fluids and tissues, as well as cardiac fluids and tissues, such that both intrathoracic and intracardiac impedance is implicated.

For each of the four electrodes of the quad-pole LV lead, the device measures impedance ($Z_i$) values between the "i-th" electrode and the SVC coil over at least one heartbeat while current is being injected. Maximum and minimum impedance values (max $Z_i$ and min $Z_i$) are determined for each heartbeat and a set of difference values ($\Delta Z_i$) are then determined based on max $Z_i$ and min $Z_i$. That is, $\Delta Z_i$=max $Z_i$–min $Z_i$, for each i. The difference values are then summed to yield a combined difference value ($\Delta Z$sum), i.e. $\Delta Z$sum=$\Sigma \Delta Z_i$, which is representative of relative changes in stroke volume. To obtain an absolute value for stroke volume (i.e. a value properly scaled to the units of stroke volume), a pre-calibrated scaling factor can be applied to $\Delta Z$sum to yield the final stroke volume estimate for the patient. This value can then be used for a wide variety of purposes such as adjusting pacing delays to maximize stroke volume and detecting or tracking heart failure, or it can simply be recorded and output as diagnostic data for clinician review. By providing an absolute value estimate of stroke volume within the patient (rather than just various numerical impedance output parameters), the clinician is thereby given important clinical information in a manner that is both useful and familiar. The clinician can then use this information to guide patient therapy decisions.

In various examples described herein, impedance measurements are used, but it should be understood that related electrical parameters might be detected and/or exploited instead, such as admittance, conductance or immittance. Those skilled in the art can convert between these related parameters. Herein, "values representative of impedance" is deemed to include related electrical parameters such as admittance, conductance and immittance.

System and method implementations of the various exemplary embodiments are presented herein.

BRIEF DESCRIPTION OF THE DRAWINGS

Features and advantages of the described implementations can be more readily understood by reference to the following description taken in conjunction with the accompanying drawings.

FIG. 9 illustrates a computer model of the heart used to assess ESV and impedance parameters for the hybrid configuration of FIG. 7;

FIG. 11 is a table illustrating various parameters associated with exemplary hybrid configurations, such as those of FIG. 7;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Medical System

Figure 1:
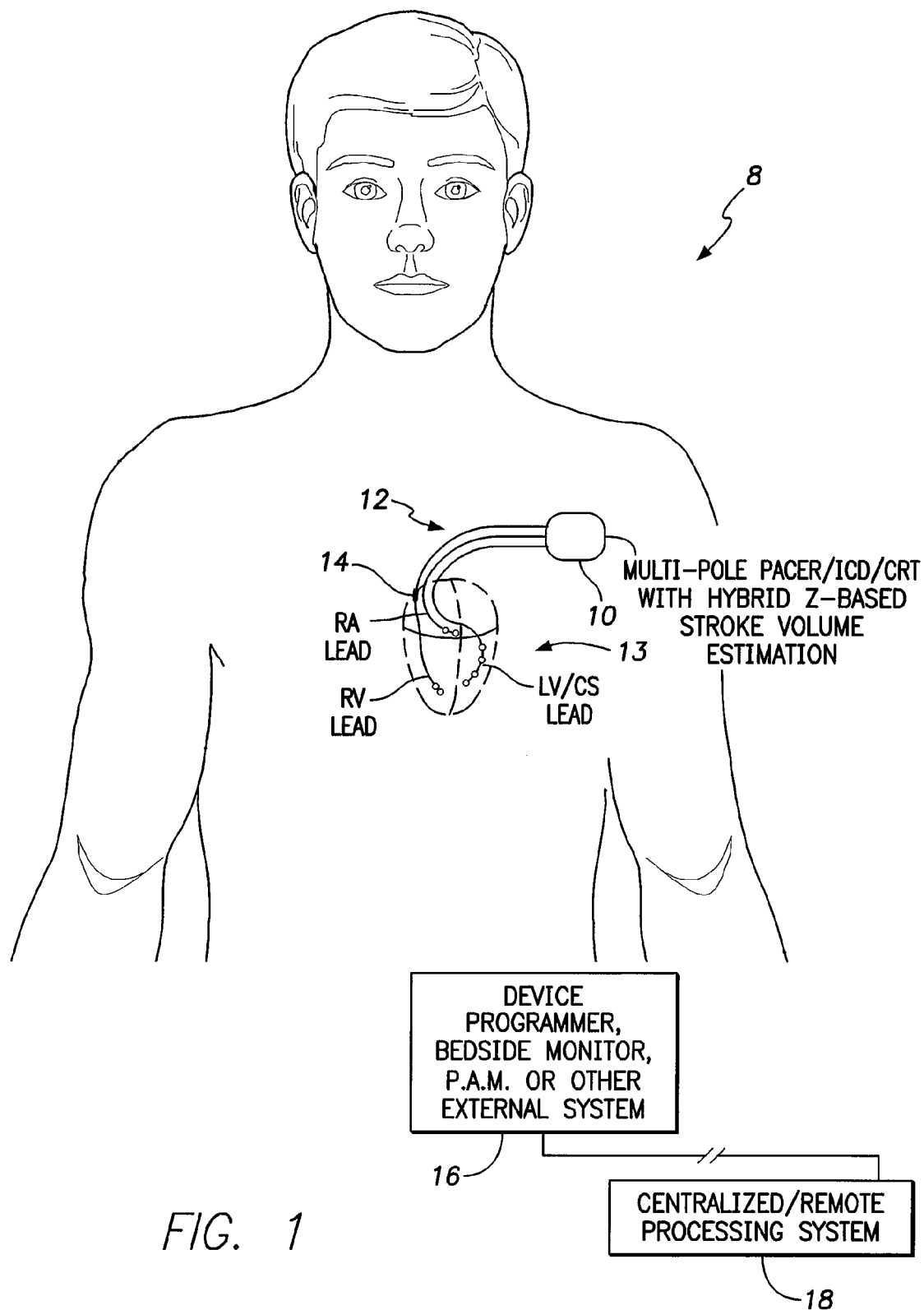
FIG. 1 illustrates pertinent components of an implantable medical system having a pacemaker, ICD or CRT device equipped to estimate stroke volume or related cardiac function parameters based on impedance signals detected within a patient via a hybrid impedance configuration.

FIG. 1 illustrates an implantable cardiac rhythm management system 8 capable of estimating or assessing stroke volume or related cardiac function parameters based on impedance measured via a hybrid configuration. The implantable system 8 includes a pacer/ICD/CRT device 10 or other cardiac rhythm management device equipped with one or more leads 12 implanted on or within the heart of the patient, including a multi-pole LV lead implanted via the coronary sinus (CS). To illustrate the multi-pole configuration of the LV lead, a set of electrodes 13 is shown distributed along the LV lead. In the examples described herein, a quad-pole (or "quadrapolar" or "quadripolar") lead is employed (such as the Quartet™ lead provided by St Jude Medical). Other suitable LV leads may instead be employed, including leads with more or fewer electrodes. Exemplary RV and RA leads are also shown that include tip/ring pairs. The RV lead includes an SVC coil 14, which can be used as a reference electrode in the hybrid configuration for injecting current. Other electrodes of various sizes and shapes may be additionally or alternatively provided, such as coil electrodes mounted in or on the LV, RV or the left atrium (LA.) See FIG. 12 for a more complete and accurate illustration of the location of various exemplary lead systems. Although identified as a pacer/ICD/CRT in FIG. 1, it should be understood that device 10 can be any suitably-equipped implantable medical device, such as a standalone pacemaker, ICD or CRT device, including CRT-D and CRT-P devices. In the following, for brevity, device 10 will be referred to simply as a pacer/ICD.

Based in the assessment of stroke volume, the pacer/ICD can then optimize pacing delays and/or detect and track heart failure or related conditions using techniques described below. Depending upon the particular conditions detected, the pacer/ICD will issue warning signals, if appropriate. For example, if a significant progression of heart failure is indicated based on changes in stroke volume, warning signals may be generated to warn the patient, either using an internal warning device (which can be part of the pacer/ICD) or using an external bedside monitor/handheld warning device 16 or other external system. The internal warning device may be a vibrating device or a "tickle" voltage device that, in either case, provides perceptible stimulation to the patient to alert the patient so that the patient may consult a physician. In one example, once the warning is felt, the patient positions an external warning device above his or her chest. The handheld device, which might be a personal advisory module (PAM), receives short-range telemetry signals from the implanted device and provides audible or visual verification of the warning signal. The handheld warning device thereby provides confirmation of the warning to the patient, who might otherwise be uncertain as to the reason for the internally generated warning signal. For further information regarding this warning/notification technique, see U.S. Pat. No. 7,272,436 to Gill et al.

If a bedside monitor is provided, the bedside monitor provides audible or visual alarm signals to alert the patient or caregivers, as well as providing textual or graphic displays. In addition, any diagnostic information pertaining to the deteriorating cardiac condition of the patient is transferred to the bedside monitor or is stored within the pacer/ICD for subsequent transmission to an external programmer for review by a clinician or other medical professional. The clinician may then prescribe therapies to address the condition. The clinician may also adjust the operation of the pacer/ICD to activate, deactivate or otherwise control any therapies that are automatically applied, including titration of medications if an implantable drug infusion pump is provided. The bedside monitor may be directly networked with an internet network site or a centralized processing system 18 for immediately notifying the clinician of any urgent medical condition. The centralized system may include such systems as Merlin.Net of St. Jude Medical, which may be used in conjunction with bedside monitors or similar devices such as the HouseCall™ remote monitoring system or the Merlin@home systems, also of St. Jude Medical.

In some implementations, the pacer/ICD itself performs the assessment of stroke volume based on impedance measurements made using its leads. In other implementations, the device transmits the measurements to the external system 16, which performs the assessment. In the following examples, it is assumed that the pacer/ICD performs the assessment using on-board components. An example where the external programmer performs the assessment described below with reference to FIG. 14.

Hence, FIG. 1 provides an overview of an implantable medical system for assessing stroke volume, optimizing pacing delays, detecting and tracking heart failure, and delivering appropriate warning/notification signals and therapy, where appropriate, etc. Embodiments may be implemented that do not necessarily perform all of these functions. For example, embodiments may be implemented that assess stroke volume but do not automatically adjust therapy. In addition, note that the particular locations of the implanted components shown in FIG. 1 are merely illustrative and may not necessarily correspond to actual implant locations.

Overview of Stroke Volume Assessment using Hybrid Configurations

Figure 2:
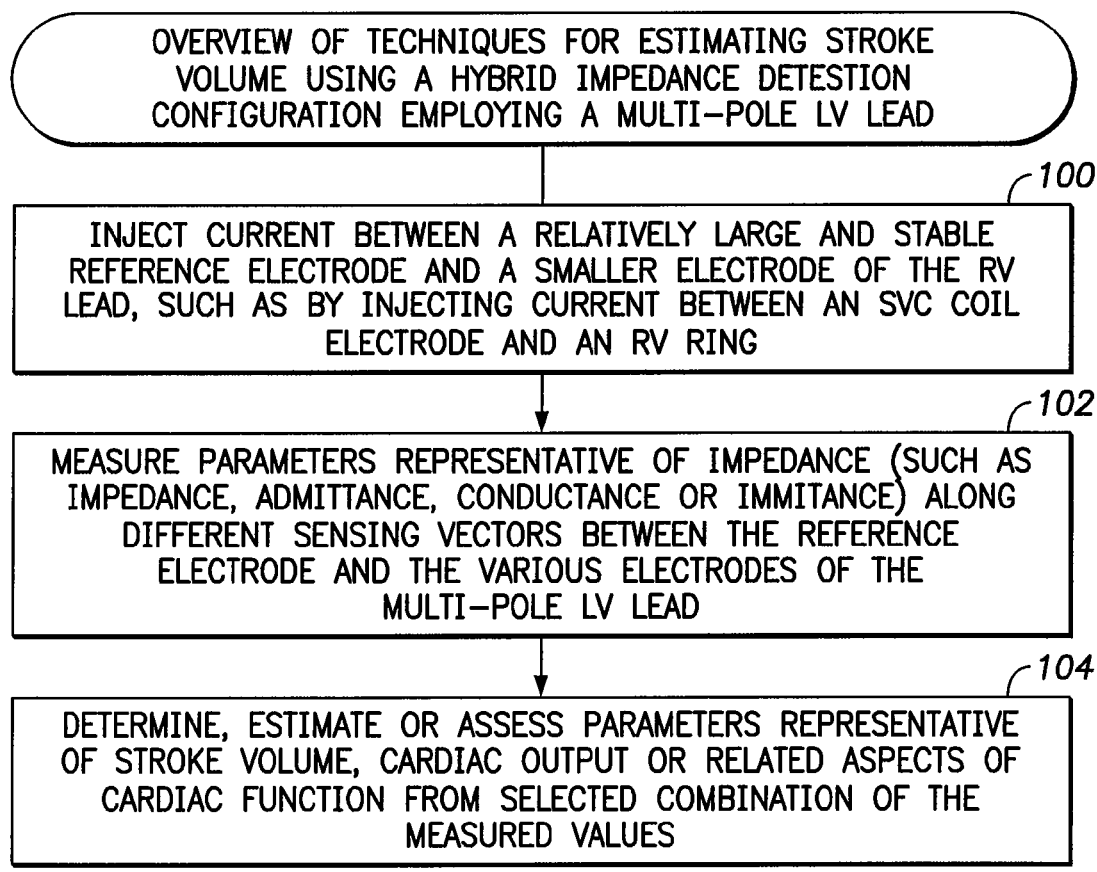
FIG. 2 provides an overview of a technique for estimating stroke volume parameters based on impedance that may be performed by the system of FIG. 1 using a hybrid impedance detection configuration.

FIG. 2 broadly summarizes the general assessing stroke volume or other parameters representative of stroke volume based on impedance that may be exploited by the components of the system of FIG. 1. Beginning at step 100, the pace/ICD injects current between a relatively large and stable reference electrode and a smaller electrode of the RV lead, such as by injecting current between the SVC coil and the RV ring. As noted, the use of the relatively large and stable SVC coil generates a relatively wide electrical field for impedance measurement purposes that is relatively insensitive to patient motion artifacts and/or changes in tissue properties. The relatively wide field encompasses at least some non-cardiac thoracic fluids and tissues, as well as cardiac fluids and tissues, such that both intrathoracic and intracardiac impedance is implicated. Exemplary electrical fields generated by current injected using an SVC coil are discussed below based on computer simulations thereof. The SVC coil is employed (in at least some examples) as the "reference" electrode due to its relatively large size and its stable location in the SVC, but other reference electrodes might instead be used so long as such electrodes are efficacious for the intended purposes described herein. For example, it might be appropriate in some cases to instead inject current using the device can rather than the SVC coil.

At step 102, the device then measures values representative of electrical impedance (such as impedance, admittance, conductance or immittance) along different sensing vectors between the reference electrode and the various tip and ring electrodes of the multi-pole LV lead. Thus, current is injected using one vector and then impedance is measured using other vectors, thereby providing for a hybrid impedance detection configuration. At step 104, the pacer/ICD then determines, estimates or assesses parameters representative of stroke volume, cardiac output or related aspects of cardiac function within the patient from a selected combination of the measured values taken along the different vectors by applying suitable conversion or scaling factors. Exemplary techniques are described below wherein a sum of impedance "difference values" obtained along the different vectors is exploited to estimate stroke volume within the patient based on predetermined scaling factors. Cardiac output can then be calculated from stroke volume and heart rate. Other cardiac function parameters might be determined as well by the device, such as EDV, ESV and EF.

Thus, FIG. 2 broadly summarizes techniques for assessing stroke volume or other aspects of cardiac function based on impedance measured using a hybrid measurement configuration.

Exemplary Stroke Volume Assessment using Hybrid Configuration

Figure 3:
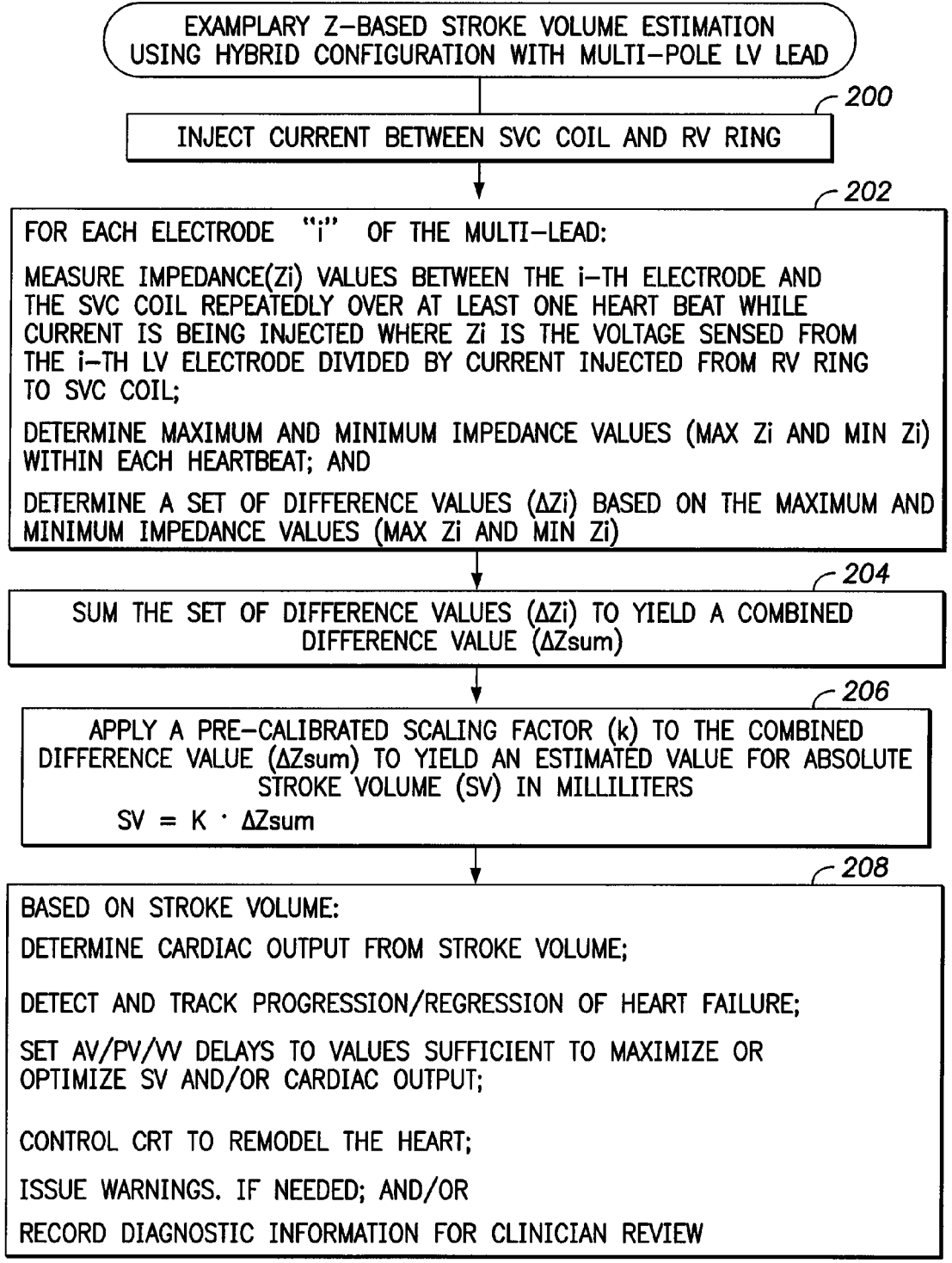
FIG. 3 illustrates an exemplary technique for use with the general technique of FIG. 2 for estimating stroke volume using impedance detected using hybrid configurations.

FIG. 3 illustrates an exemplary technique for estimating stroke volume based on impedance measured using a hybrid configuration exploiting the SVC coil along with a multi-pole LV lead. At step 200, the pacer/ICD injects current between the SVC coil and the RV ring. Exemplary injection current values are discussed below with reference to results of computer simulations. At step 202, for each electrode "i" of the multi-pole LV lead, the device: measures impedance ($Z_i$) values between the i-th electrode and the SVC coil repeatedly over at least one heartbeat where $Z_i$ is the voltage sensed from the i-th LV electrode divided by current injected from RV ring to SVC coil; determines maximum and minimum impedance values (max $Z_i$ and min $Z_i$) within each heartbeat (i.e. the device assess impedance at end diastolic and end systolic points within the heartbeat); and then determines a set of difference values ($\Delta Z_i$) based on the maximum and minimum impedance values (max $Z_i$ and min $Z_i$) by subtracting the min $Z_i$ values (i.e. the end diastolic values) from the corresponding max $Z_i$ values (i.e. the end systolic values), or min $Z_i$ and max $Z_i$ over a heartbeat for a couple of beats. For a quad-pole example, the device therefore measures impedance along four vectors (SVC-D1, SVC-M2, SVC-M3 and SVC-P4) throughout the heartbeat while current is being applied and then determines four impedance difference values ($\Delta Z_{SVC-D1}$, $\Delta Z_{SVC-M2}$, $\Delta Z_{SVC-M3}$, $\Delta Z_{SVC-P4}$). As can be appreciated, data may be collected over multiple heartbeats and averaged together to provide a more robust determination of the difference values.

At step 204, the device then selectively combines the impedance values by summing the set of difference values ($\Delta Z_i$) to yield a combined difference value ($\Delta Z\text{sum}$), i.e. $\Delta Z\text{sum}=\Sigma\Delta Z_i$. Alternatively, within steps 202 and 204, other procedures or algorithms may be performed to calculate $\Delta Z\text{sum}$. For example, rather than taking the difference of the individual min and max values and then summing the difference values, the device could instead sum the min values, sum the max values, and then take the difference of the resulting sums to yield a value equivalent to $\Delta Z\text{sum}$.

At step 206, to obtain an absolute value for stroke volume (i.e. a value properly scaled to the units of stroke volume), the device applies a pre-calibrated scaling factor or correlation factor (k) to the combined difference value ($\Delta Z\text{sum}$) to yield an estimated value for absolute stroke volume (SV) in milliliters (or any other appropriate units):

$$SV=k\cdot\Delta Z\text{sum}.$$

In one example, the determine the value for "k", values for $\Delta Z$sum are obtained within the patient for comparison again known values for stroke volume detected using a reference detection technique such as an echocardiographic technique, ultrasound, etc. The values for $\Delta Z$sum and the known stroke volume values are correlated with one another to determine a suitable value for "k" that can then be applied to $\Delta Z$sum obtained within the patient during device usage. As can be appreciated, more sophisticated correlation equations/techniques might instead be used—such as exponential, polynomial or other non-linear techniques—to provide a more precise estimate of stroke volume. Also, different scaling factors might be determined for use with different patient postures, heart rates, etc. Hence, the example of step 206 should be regarded as merely illustrative.

At step 208, the device then exploits the estimate of stroke volume to: determine cardiac output; detect and track progression/regression of heart failure; optimize AV/PV/VV delays to maximize or otherwise improve stroke volume; control CRT to remodel the heart; issue warnings, if needed, perhaps in response to a significant progression of heart failure; and/or record diagnostic information for clinician review. Cardiac output can be easily derived from stroke volume based on heart rate. Progression of heart failure may be indicated based on a significant drop in stroke volume/cardiac output over time (in the absence of other factors that might affect stroke volume/cardiac output such as changes in activity levels, pacing rates, medications, etc.) Conversely, regression heart failure may be indicated based on significant increase in stroke volume/cardiac output over time (again, in the absence of other "confounding" factors.)

Insofar as the optimization of AV/PV/VV delays are concerned, these delay values may be adjusted while monitoring stroke volume/cardiac output to determine delay values sufficient to maximize (or at least improve) stroke volume and/or cardiac output. This may be performed in conjunction with other optimization techniques. See, for example, the following patents and patent applications that set forth various systems and methods for determining and/or adjusting AV/PV/VV pacing delays: U.S. Pat. No. 7,590,446 of Min et al.; U.S. Published Patent Application 2009/0299423A1; U.S. patent application Ser. No. 11/952,743, filed Dec. 7, 2007, entitled "Systems and Methods for Determining Optimal Atrio-Ventricular Pacing Delays using either Paced or Sensed Atrial Beats"; U.S. patent application Ser. No. 12/328,605, filed Dec. 4, 2008, entitled "Systems and Methods for Controlling Ventricular Pacing in Patients with Long Intra-Atrial Conduction Delays"; U.S. patent application Ser. No. 12/507,646, filed Jul. 22, 2009, of Min et al. entitled "Systems and Methods for Optimizing Ventricular Pacing Delays for use with Multi-Pole Leads"; U.S. patent application Ser. No. 12/639,881, filed Dec. 16, 2009, of Min et al., entitled "Systems and Methods for Determining Ventricular Pacing Sites for use with Multi-Pole Leads"; U.S. patent application Ser. No. 12/604,280, filed Oct. 22, 2009, of Min et al., entitled "Systems and Methods for Determining Optimal Electrode Pairs for use in Biventricular Pacing using Multi-Pole Ventricular Leads"; U.S. patent application Ser. No. 12/957,142, filed Nov. 30, 2010, of Min, entitled "Systems and Methods for Determining Optimal Atrioventricular Pacing Delays based on Cardiomechanical Delays"; and U.S. patent application Ser. No. 12/976,322, filed Dec. 22, 2010, 2010, of Min et al., entitled "Systems and Methods for Optimizing AV/VV Pacing Delays using Combined IEGM/Impedance-based Techniques for use with Implantable Medical Devices". See, also, U.S. Pat. No. 7,248,925, to Bruhns et al., entitled "System and Method for Determining Optimal Atrioventricular Delay based on Intrinsic Conduction Delays." At least some of the techniques are implemented within the QuickOpt™ systems of St. Jude Medical.

It should be understood that the "optimal" delays obtained using the techniques described herein are not necessarily absolutely optimal in a given quantifiable or mathematical sense. What constitutes "optimal" depends on the criteria used for judging the resulting performance, which can be subjective in the minds of some clinicians. The pacing delays determined by the techniques described herein represent, at least, "preferred" delays. Clinicians may choose to adjust or alter the selection of the delays for particular patients, at their discretion.

CRT techniques may be employed in an effort to remodel the heart to improve stroke volume/cardiac output. Briefly, CRT seeks to normalize asynchronous cardiac electrical activation and resultant asynchronous contractions associated with heart failure by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis at al., entitled "Multi-Electrode Apparatus and Method for Treatment of Congestive Heart Failure"; U.S. Pat. No. 6,628,988 to Kramer at al., entitled "Apparatus and Method for Reversal of Myocardial Remodeling with Electrical Stimulation"; and U.S. Pat. No. 6,512,952 to Stahmann at al., entitled "Method and Apparatus for Maintaining Synchronized Pacing".

Insofar as the diagnostic information to be recorded for clinician review is concerned, the device can record the estimated stroke volume/cardiac values, as well as any of the intermediate impedance values determined by the device (such as the various maximum or minimum impedance values or their difference values). This information may be recorded along with device operational data (such as the current pacing configuration, pacing rate, etc.) and patient physiological/anatomical data (such as current posture, heart rate, blood pressure, etc.), assuming such information is available.

As already explained, rather than detecting impedance, other related electrical signals or parameters can instead be exploited, such as admittance, conductance, immittance or their equivalents, where appropriate.

The various techniques described herein may be exploited in conjunction with other assessment techniques. See, for example, U.S. Pat. No. 12/975,085, filed Dec. 21, 2010, of Rosenberg et al., entitled "Systems and Methods for Assessing the Sphericity and Dimensional Extent of Heart Chambers for use with an Implantable Medical Device." See, also, the near-field impedance techniques set forth in: U.S. patent application Ser. No. 12/853,130, filed Aug. 9, 2010, of Gutfinger et al., entitled "Near Field-Based Systems and Methods for Assessing Impedance and Admittance for use with an Implantable Medical Device" and related applications.

Depending upon the particular implementation, some or all of the steps of the various figures are performed by the implantable device itself. Additionally or alternatively, at least some of the steps can be performed by an external programmer or other external system based on impedance or other data measured within the patient and then transmitted to the external device.

Computer Simulations of Exemplary Hybrid Configurations

Turning now to FIGS. 4-11, the results of computer simulations of three different hybrid configurations are discussed. In these simulations, a bipolar LV lead was used rather than a multi-polar LV lead but many of the observations made using these simulations are expected to apply to multi-pole lead configurations. In the first hybrid configuration, Config 1, current is injected RV tip to RV ring and voltage is measured LV tip to LV ring. In the second hybrid configuration, Config 2, current is injected RV tip to LV ring and voltage is measured RV ring to LV tip. In the third hybrid configuration, Config 3, current is injected SVC coil to RV ring and voltage is measured from the LV tip and ring electrodes to the SVC coil.

Figure 4:
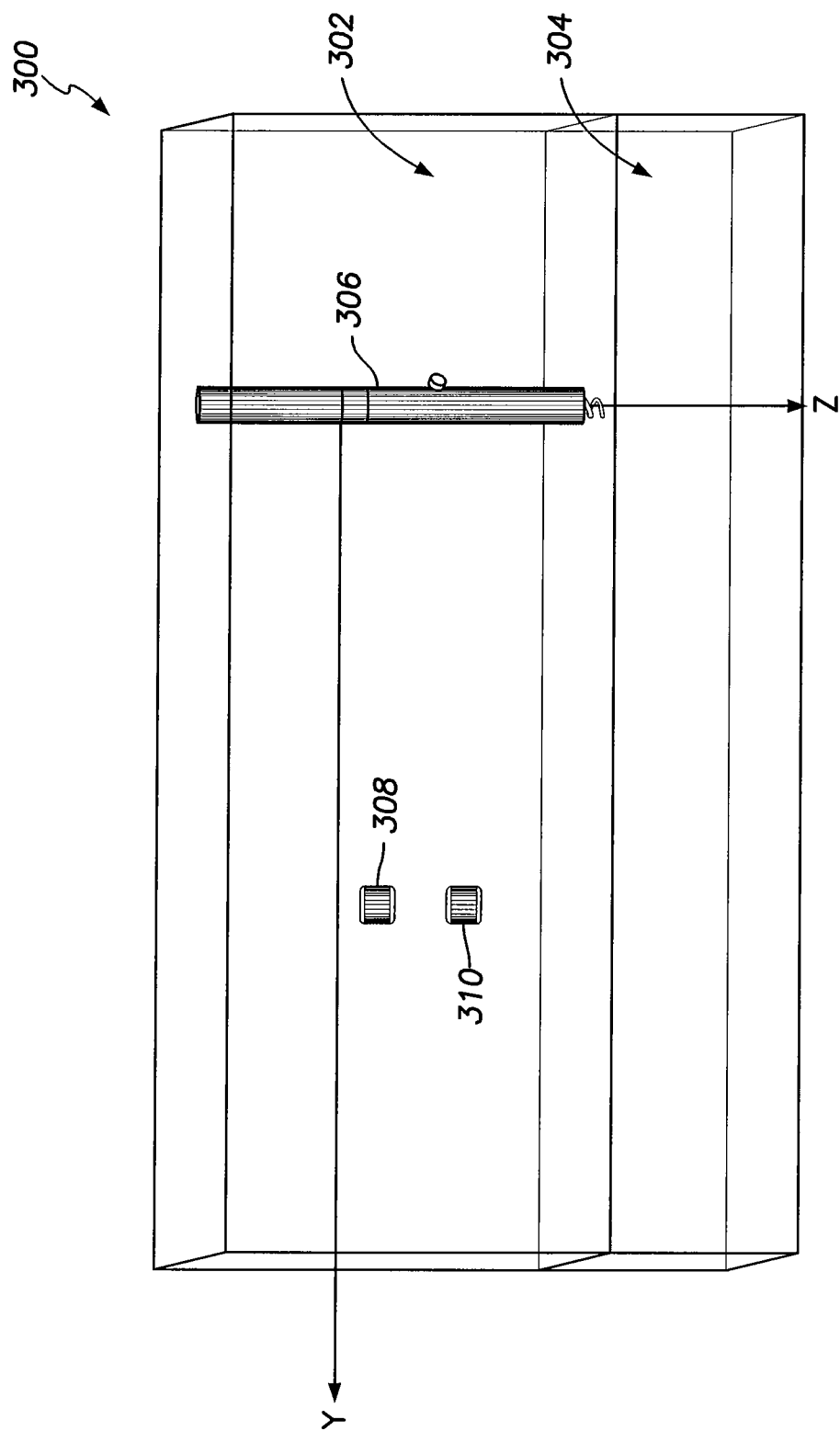
FIG. 4 illustrates a tissue bath model used to investigate the efficacy of different hybrid configurations.

The simulations employed a "tissue bath" model. A portion of one such model 300 is shown in FIG. 4. Briefly, the 3-D model employs a representation of blood 302 over myocardial tissue 304. Pertinent portions of an LV lead 306 are also represented, which in this example includes a fixed LV tip and LV ring pair. The model also provides RV ring and RV tip electrodes, 308 and 310, respectively. In this model, the spacing between RV tip and RV ring is fixed. Likewise, the spacing between LV tip and LV ring is fixed. However, the distance/spacing between the LV pair and the RV pair can be varied to assess voltage differences.

Figure 5:
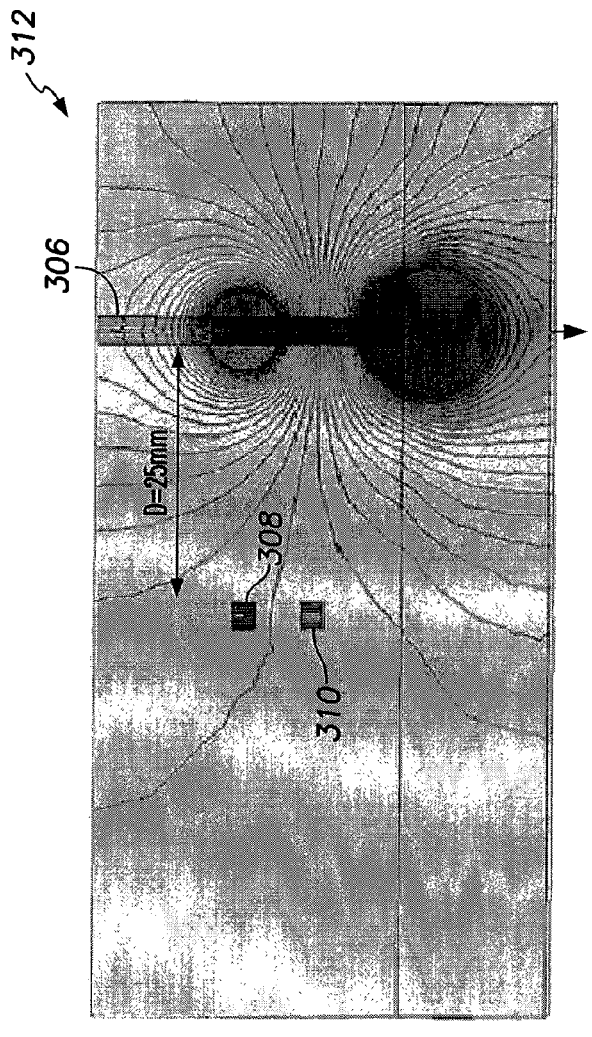
FIG. 5 illustrates an iso-electric map generated based on the tissue bath model of FIG. 4 for a first hybrid configuration (Config 1) wherein current is injected RV tip to RV ring and voltage is measured LV tip to LV ring.

FIG. 5 illustrates an iso-electrode voltage map 312 for Config 1 wherein the spacing between the LV and RV electrodes was set to 25 mm (and with LVRgprx=−1.52 V and LVRgdis=−1.535 V where LVRgprx refers to the LV ring proximal electrode and LVRgdis refers to the LV ring distal electrode.) Note that in this bipolar example the LV ring distal electrode (LVRgdis) can also be referred to as the "LV tip" electrode. The voltage applied was 7.5 V where R=7.5 V/I and Intra-R=dv/I and dV=LVdis−LVprox; P=total power; and I=total current. Simulations for Config 1 showed that as the spacing between LV and RV electrodes increased, Intra-R decreased. From the iso-voltage lines, the change in voltage with electrode position depends highly on where the electrode is located. For example with LVRgdis, the change in voltage was much smaller as spacing varied from 15 mm, 25 mm and 35 mm compared with LVRgprox. Table 313 provides details for three exemplary spacings (D=15 mm, D=25 mm, and D=35 mm.) As can be seen, the sensing electrodes are relatively insensitive to spacing. For example, the voltage on LVRgdis did not change much as spacing was varied from 15 mm, 25 mm and 35 mm. As such, this configuration is not likely to be effective in sensing impedance changes representative of expansion or contraction of the LV associated with changes in stroke volume.

Figure 6:
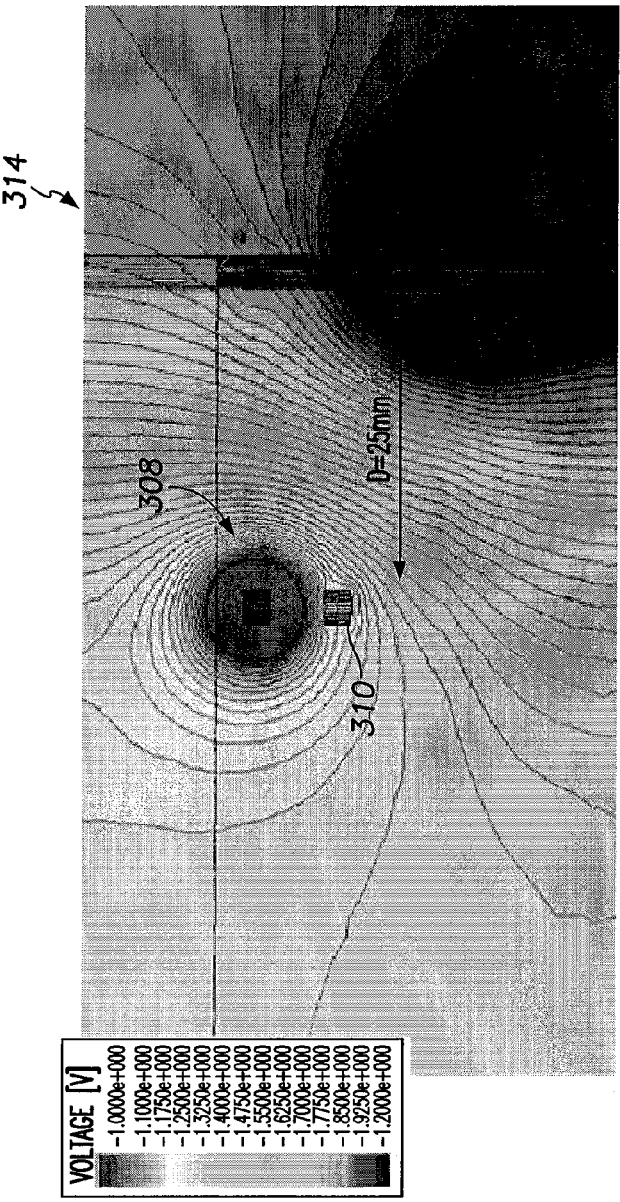
FIG. 6 illustrates an iso-electric map generated based on the tissue bath model of FIG. 4 for a second hybrid configuration (Config 2) wherein current is injected RV tip to LV ring and voltage is measured RV ring to LV tip.

FIG. 6 illustrates an iso-electrode voltage map 314 for Config 2 wherein the spacing between the LV and RV electrodes was also set to 25 mm.

Again, the voltage applied was 7.5 V where R=7.5 V/I and Intra-R=dv/I and dV=RVrg−LVrgdis; P=total power; and I=total current. With Config 2, as distance increased, Intra-R increased. Since the spacings between RV tip and RV ring (or between LV tip and LV ring) are fixed, the voltage changes on the sensed pair (RV ring and LV ring prox) came from the changes in distance/spacing between LV and RV electrodes. Table 315 provides details for the three exemplary spacings (D=15 mm, D=25 mm, and D=35 mm.) The voltage drops more rapidly around the source electrode pair locally than elsewhere. As spacing varies, the sensed voltage at the electrodes depends largely on the voltage gradient change. This would make extensions to multi-pole LV electrodes difficult.

Moreover, with both Config 1 and Config 2, it would likely be difficult to predict stroke volume since these configurations are sensitive to local motion and depend on the relative location to voltage map. If one wanted to extend these hybrid configurations to quadra-pole LV leads, it would not be clear how to extract useful stroke volume information.

Figure 7:
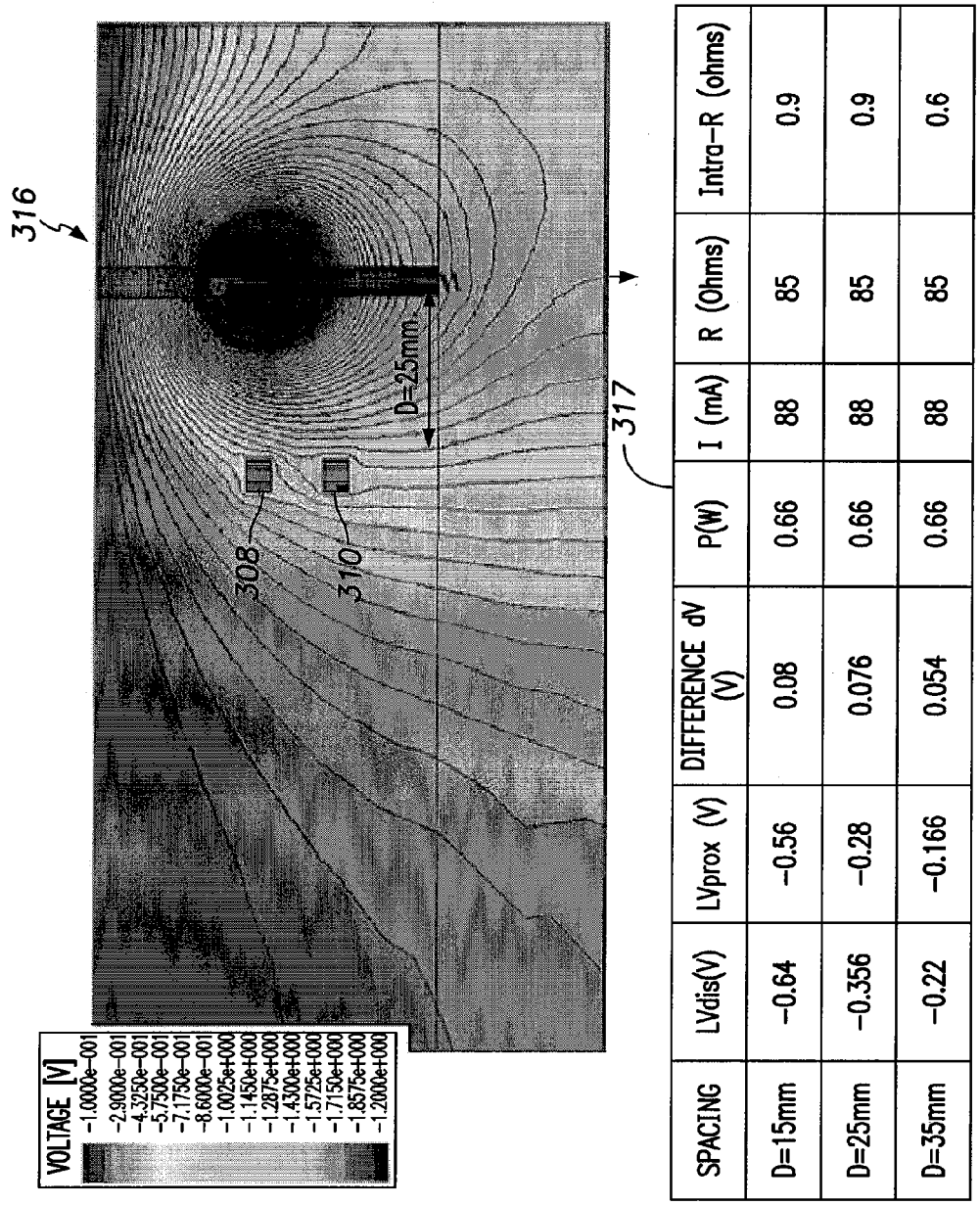
FIG. 7 illustrates an iso-electric map generated based on the tissue bath model of FIG. 4 for a third and preferred hybrid configuration wherein current is injected SVC coil to RV ring and voltage is measured with the SVC coil.

FIG. 7 illustrates an iso-electrode voltage map 316 for Config 3 wherein the spacing between the LV and RV electrodes was 25 mm. Again, the voltage applied was 7.5 V where R=7.5 V/I and Intra-R=dv/I and dV=RVrg−LVrgdis; P=total power; and I=total current. Table 317 provides details for the same three exemplary spacings (D=15 mm, D=25 mm, and D=35 mm.) The SVC was simulated as the top of the tank of the tissue bath. Using conventional techniques to compute Intra-R showed only small changes near the SVC. However, voltage at both locations of LV dis and LV prox leads changed consistently as the spacing (D) changed from D=15 mm, 25 mm and 35 mm, indicating that this configuration is useful for assessing changes in stroke volume. As shown in Table 317, the changes in voltage with spacing change in parallel for the two LV electrodes. Although the simulation results of FIG. 7 are for a bipolar LV lead, similar behaviors are expected for multi-pole LV electrodes.

Figure 8:
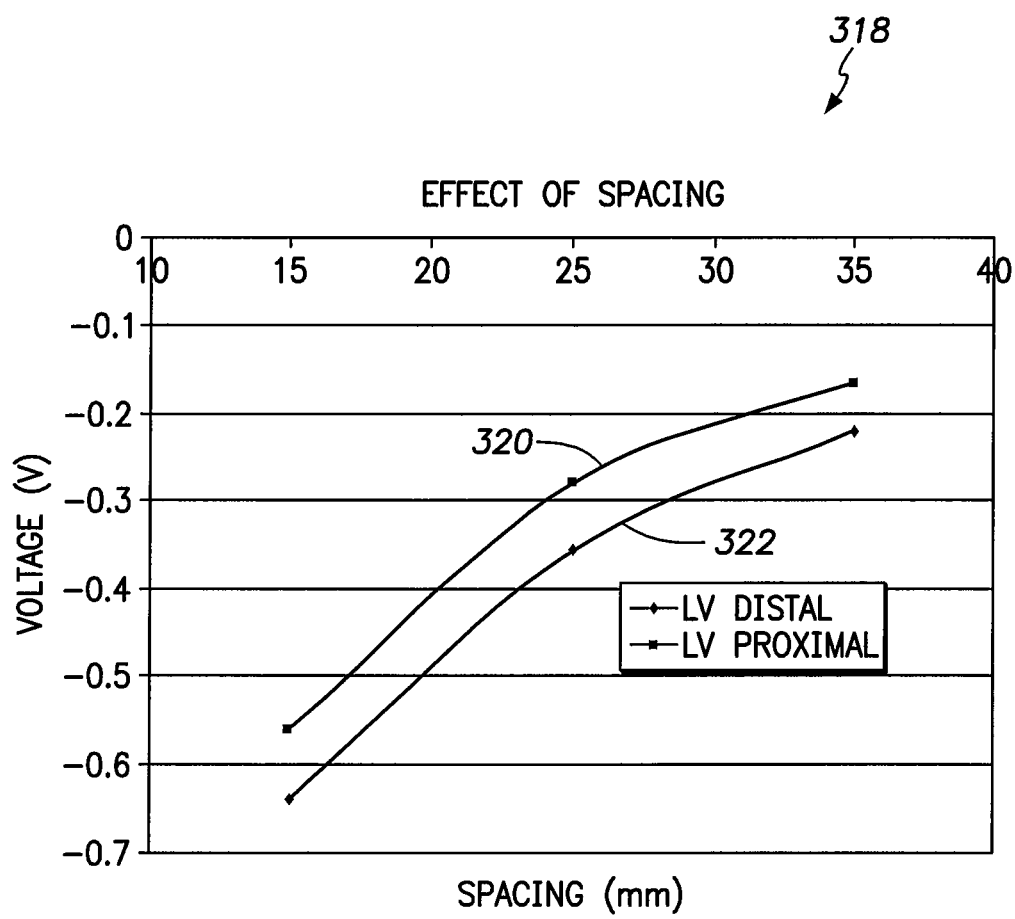
FIG. 8 illustrates the effect of electrode spacing on sensed voltage for the hybrid configuration of FIG. 7.

FIG. 8 illustrates the effect of electrode spacing on sensed voltage for Config 3. These are simulated results based on current injection RV ring to SVC coil with voltage sensed at LVdis-SVC and LVprx-SVC, with the SVC simulated as the top of the tank. More specifically, the figure provides a graph 318 showing voltage vs. spacing at an LV proximal location 320 and an LV distal location 322. As can be seen, there is a fairly uniform and predictable change in voltage with change in spacing, which is useful for assessing stroke volume or related cardiac function parameters.

The results of FIG. 8 were obtained based on computer model simulations. More specifically, a pair of computer models of the heart were created, one for the heart at the end systolic phase of the heartbeat and another for the heart at the end diastolic phase of the heartbeat. Cardiac computed tomography (CT) images of a patient were used to create the 3D heart models, which include all four chambers, the SVC, the pulmonary artery (PA), and the aorta, one at end of systolic and the other at end diastolic. These models are shown in FIGS. 9 and 10.

FIG. 9 shows the end systolic heart model both in a finite element analysis (FEA) model with surface meshes 400 and a CT rendered representation 402. This model represents heart chambers, SVC, PA and the aorta at the end of systole, with a pair of RV electrodes, an SVC coil, and a pair of LV electrodes implanted therein. The electrode pairs are shown by way of reference numerals 404 for the LV pair and 406 for the RV pair.

Figure 10:
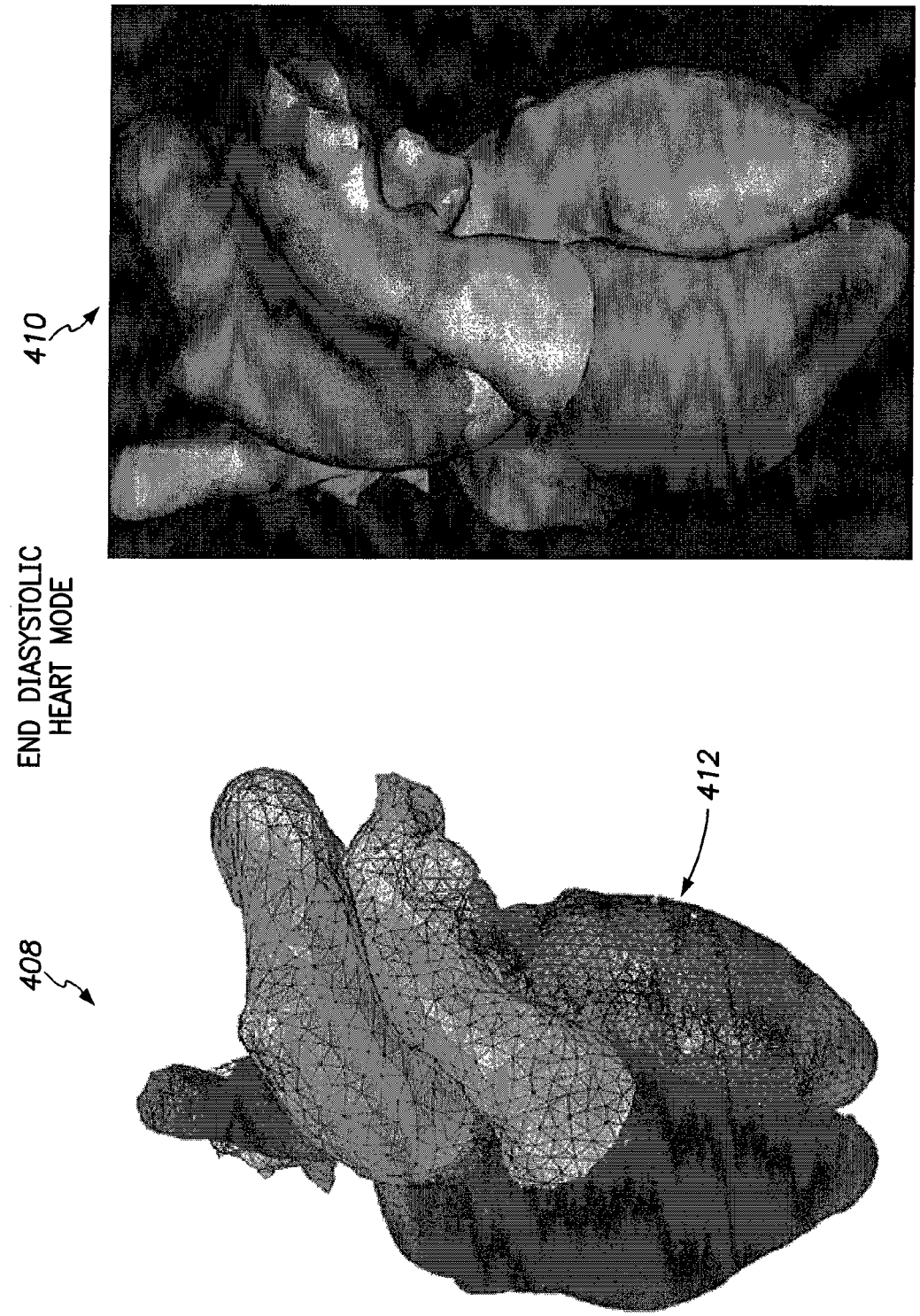
FIG. 10 illustrates a computer model of the heart used to assess EDV and impedance parameters for the hybrid configuration of FIG. 7.

FIG. 10 shows the end diastolic heart model both an FEA model with surface meshes 408 and a CT rendered representation 410. This model represents heart chambers, SVC, PA and the aorta at the end of diastole, with a pair of RV electrodes, an SVC coil, and a pair of LV electrodes implanted therein. The LV pair is shown by way of reference numeral 410; the other pair is obscured in this view of the model. As can be seen from a comparison of FIGS. 9 and 10, the configuration of the heart is quite different between end systolic and end diastolic and the relative locations and spacings of the LV and RV pairs of electrodes are different as well.

FIG. 11 provides further simulation results obtained using these computer models by way of a pair of tables 414 and 422. Table 414 includes modeling data for Config 3 where current is injected RV ring to SVC coil while sensing voltage from LV electrodes. Impedance difference values obtained between an LV distal electrode (LVdisR) and the SVC coil are shown along with impedance values obtained between an LV proximal electrode (LVproxR) and the SVC coil for an example where a 50V injection current was applied. Values for End Systolic and End Diastolic were calculated based on the models. The End Systolic LV disR and LV proxR values were added together to yield summed End Systolic value 416. Likewise, the End Diastolic LV disR and LV proxR values were added together to yield summed End Diastolic value 418. The difference between the two summed values 420, which is about 6%, can then be used as a proxy to track changes in stroke volume. The larger the percentage difference, the greater the correlation between the summed impedance values and stroke volume. For comparison, corresponding difference percentages for a configuration when impedance is measured SVC—can is only about 1.4%. The table also shows percentage differences for various other values corresponding to End Systolic and End Diastolic phase, such as difference values based on resistance (R) and current (I), which are both about 8%, where total R is V across RV ring and SVC coil divided by the current through them.)

Table 422 includes modeling data for an alternative configuration where current is instead injected RV ring to Can while sensing from the LV electrodes (again using a 50V injection current). As can be seen from the table, the difference between the End Systolic and End Diastolic values is about 4% (rather than 6% when using the SVC). Also, note that the difference in impedance for this configuration is about 7% (as represented by the difference in R (ohms) between End Systolic and End Diastolic) as compared to about 8% when using the SVC.

In view of the foregoing observations and considerations, when using a multi-pole hybrid configuration it is desirable to select a relatively stable reference electrode, such as SVC, and to then exploit multiple sensing vectors between the reference electrode and each of the individual electrodes (i.e., LVi to SVC) while injecting current to RV ring to SVC. Insofar as the reference electrode is concerned, the less subject it is to patient motion and tissue property changes, the better the performance should be.

Although primarily described with respect to examples having a pacer/ICD equipped with a quad-pole lead, other implantable medical devices and lead systems may instead be equipped to exploit the techniques described. For the sake of completeness, an exemplary pacer/ICD/CRT device will now be described, which includes components for performing the functions and steps already described.

Exemplary Pacer/ICD/CRT with Quad-Pole Lead

Figure 12:
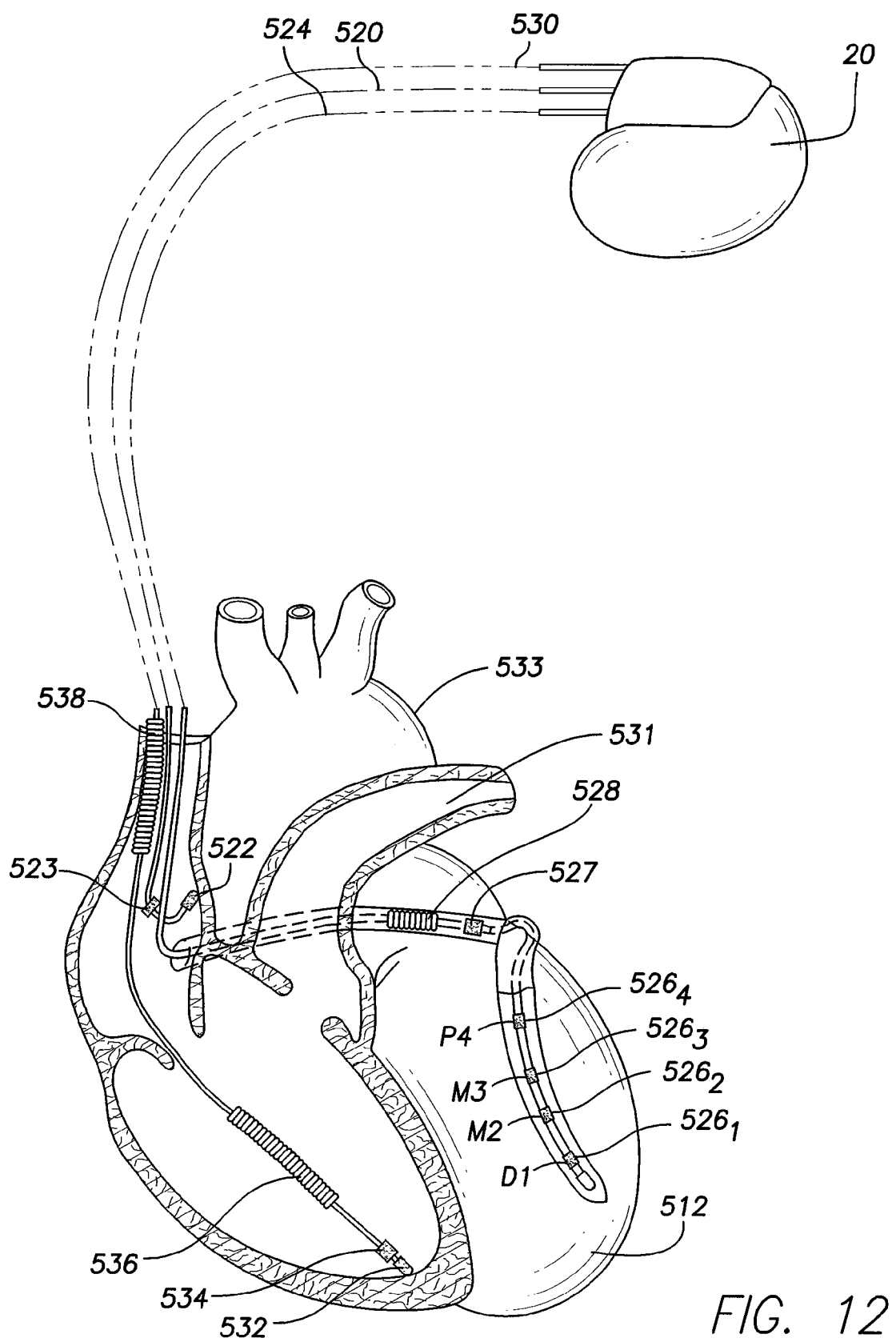
FIG. 12 is a simplified, partly cutaway view, illustrating the device of FIG. 1 along with at set of leads implanted in or on the heart of the patient.
Figure 13:
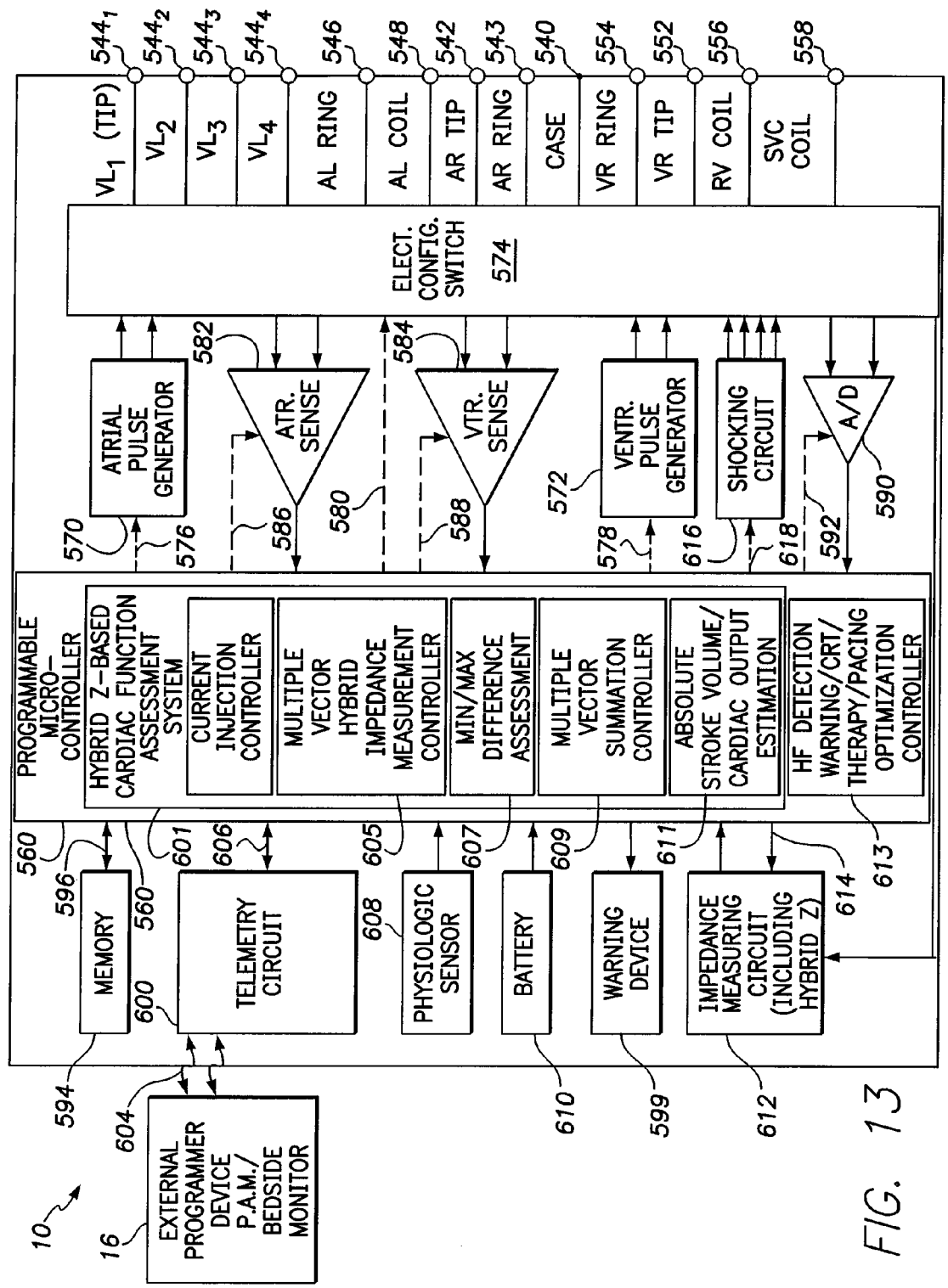
FIG. 13 is a functional block diagram of the pacer/ICD of FIG. 12, illustrating basic circuit elements that provide cardioversion, defibrillation and/or pacing stimulation in the heart and particularly illustrating on-board components for performing the various stroke volume estimation techniques.

With reference to FIGS. 12 and 13, a description of an exemplary pacer/ICD/CRT will now be provided. FIG. 12 provides a simplified block diagram of the device, which is a dual-chamber stimulation device capable of treating both fast and slow arrhythmias with stimulation therapy, including cardioversion, defibrillation, and pacing stimulation, and also capable of assessing stroke volume, as discussed above, and controlling functions in response thereto. To provide other atrial chamber pacing stimulation and sensing, device 10 is shown in electrical communication with a heart 512 by way of a left atrial lead 520 having an atrial tip electrode 522 and an atrial ring electrode 523 implanted in the atrial appendage. Device 10 is also in electrical communication with the heart by way of a right ventricular lead 530 having, in this embodiment, a ventricular tip electrode 532, a right ventricular ring electrode 534, a right ventricular (RV) coil electrode 536, and a superior vena cava (SVC) coil electrode 538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, device 10 is coupled to a multi-pole LV lead 524 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 524 is designed to receive atrial and ventricular cardiac signals and to deliver left ventricular pacing therapy using a set of four left ventricular electrodes $526_1$, $526_2$, $526_3$, and $526_4$ (thereby providing a quad-pole lead), left atrial pacing therapy using at least a left atrial ring electrode 527, and shocking therapy using at least a left atrial coil electrode 528 implanted on or near the left atrium. In other examples, more or fewer LV electrodes are provided. Although only three leads are shown in FIG. 12, it should also be understood that additional leads (with one or more pacing, sensing and/or shocking electrodes) might be used and/or additional electrodes might be provided on the leads already shown, such as additional electrodes on the RV lead.

A simplified block diagram of internal components of device 10 is shown in FIG. 12. While a particular device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 540 for device 10, shown schematically in FIG. 13, is often referred to as the "can," "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, $544_1$-$544_4$, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 523. To achieve left chamber sensing, pacing and shocking, the connector includes a left ventricular tip terminal ($VL_1$ TIP) $544_1$ and additional LV electrode terminals $544_2$-$544_4$ for the other LV electrodes of the quadra-pole LV lead.

The connector also includes a left atrial ring terminal ($A_L$ RING) 546 and a left atrial shocking terminal ($A_L$ COIL) 548, which are adapted for connection to the left atrial ring electrode 527 and the left atrial coil electrode 528, respectively. To support right chamber sensing, pacing and shocking, the connector further includes a right ventricular tip terminal ($V_R$ TIP) 552, a right ventricular ring terminal ($V_R$ RING) 554, a right ventricular shocking terminal ($V_R$ COIL) 556, and an SVC shocking terminal (SVC COIL) 558, which are adapted for connection to the right ventricular tip electrode 532, right ventricular ring electrode 534, the $V_R$ coil electrode 536, and the SVC coil electrode 538, respectively.

At the core of device 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 13, an atrial pulse generator 570 and a ventricular pulse generator 572 generate pacing stimulation pulses for delivery by the right atrial lead 520, the right ventricular lead 530, and/or the LV lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 582 and ventricular sensing circuits 584 may also be selectively coupled to the right atrial lead 520, LV lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control, automatic sensitivity control bandpass filtering, and a threshold detection circuit, as known in the art, to selectively sense the cardiac signal of interest. The automatic gain/sensitivity control enables device 10 to deal effectively with the difficult problem of sensing the low amplitude signal characteristics of atrial or ventricular fibrillation. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, device 10 utilizes the atrial and ventricular sensing circuits, 582 and 584, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 590. The data acquisition system 590 is configured to acquire intracardiac electrogram signals, convert the raw analog data into a digital signal, and store the digital signals for later processing and/or telemetric transmission to an external device 602. The data acquisition system 590 is coupled to the right atrial lead 520, the LV lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of device 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable device 10 may be non-invasively programmed into the memory 594 through a telemetry circuit 600 in telemetric communication with the external device 602, such as a programmer, transtelephonic transceiver or a diagnostic system analyzer. The telemetry circuit 600 is activated by the microcontroller by a control signal 606. The telemetry circuit 600 advantageously allows intracardiac electrograms and status information relating to the operation of device 10 (as contained in the microcontroller 560 or memory 594) to be sent to the external device 602 through an established communication link 604. Device 10 further includes an accelerometer or other physiologic sensor 608, commonly referred to as a "rate-responsive" sensor because it is typically used to adjust pacing stimulation rate according to the exercise state of the patient. However, the physiological sensor 608 may further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, AV delay, VV delay, etc.) at which the atrial and ventricular pulse generators, 570 and 572, generate stimulation pulses. While shown as being included within device 10, it is to be understood that the physiologic sensor 608 may also be external to device 10, yet still be implanted within or carried by the patient. A common type of rate responsive sensor is an activity sensor incorporating an accelerometer or a piezoelectric crystal, which is mounted within the housing 540 of device 10. Other types of physiologic sensors are also known, for example, sensors that sense the oxygen content of blood, respiration rate and/or minute ventilation, pH of blood, ventricular gradient, etc. Still further, the sensor may be equipped to detect left atrial pressure (LAP), left ventricular pressure (LVP), right ventricular pressure (RVP), photoplethysmography (PPG) or S1 heart sounds. It should be understood that multiple separate sensors can be provided and, depending upon the parameter to be detected, at least some of the sensor might be positioned external to the device housing.

The device additionally includes a battery 610, which provides operating power to all of the circuits shown in FIG. 13. The battery 610 may vary depending on the capabilities of device 10. If the system only provides low voltage therapy, a lithium iodine or lithium copper fluoride cell typically may be utilized. For device 10, which employs shocking therapy, the battery 610 should be capable of operating at low current drains for long periods, and then be capable of providing high-current pulses (for capacitor charging) when the patient requires a shock pulse. The battery 610 should also have a predictable discharge characteristic so that elective replacement time can be detected. Accordingly, appropriate batteries are employed.

As further shown in FIG. 13, device 10 is shown as having an impedance measuring circuit 612, which is enabled by the microcontroller 560 via a control signal 614. Uses for an impedance measuring circuit include, but are not limited to, detecting cardiogenic impedance for the purposes of detecting the onset of isovolumic ventricular contraction; lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; detecting the opening of heart valves; assessing stroke volume and other aspects of cardiac function as discussed above, etc. The impedance measuring circuit 612 is advantageously coupled to the switch 674 so that any desired electrode may be used, including the aforementioned hybrid configurations.

In the case where device 10 is intended to operate as an ICD device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-10 joules) or high energy (11 to 40 joules or more), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 14. The housing 540 may act as an active electrode in combination with the RV electrode 536, or as part of a split electrical vector using the SVC coil electrode 14 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia.

Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 560 is capable of controlling the synchronous or asynchronous delivery of the shocking pulses.

The microcontroller includes an on-board hybrid Z-based cardiac function assessment system 601 operative to perform or control all or some of the assessment techniques described above, particularly the aforementioned stroke volume assessment. Assessment system 601 includes a current injection controller operative to control the injection of current between the SVC coil (or other reference electrode) and the RV ring (or other electrode in the RV.) A multiple vector hybrid impedance measurement controller 605 is operative to measure values representative of impedance along different sensing vectors between the SVC reference electrode and the electrodes of the multi-pole LV lead over at least one heartbeat while the current is being injected. A min/max difference assessment system 607 is operative to determine maximum and minimum impedance values (max Zi and min Zi) with each heartbeat and determine a set of difference values ($\Delta Zi$) based on the maximum and minimum impedance values (max Zi and min Zi). A multiple vector summation controller 609 is operative to sum the set of difference values ($\Delta Zi$) to yield a combined difference value ($\Delta Z$sum) for use as a proxy or surrogate for stroke volume or other selected cardiac function parameters. An absolute stroke volume/cardiac output estimation system 611 is operative apply a scaling factor to the combined difference value ($\Delta Z$sum) to yield an estimate of the absolute stroke volume in the appropriate units.

The microcontroller also includes an HF detection/warning/CRT/ therapy/pacing optimization controller 613 operative to perform or control all or some of the functions described above in response to the estimate of stroke volume, such as detecting a tracking HF, generating warnings, controlling CRT, optimizing pacing delay parameters, etc. An internal warning device 599 may be provided for generating perceptible warning signals to the patient via vibration, voltage or other methods. Diagnostic data may be recorded in memory 594.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary External Programmer

Figure 14:
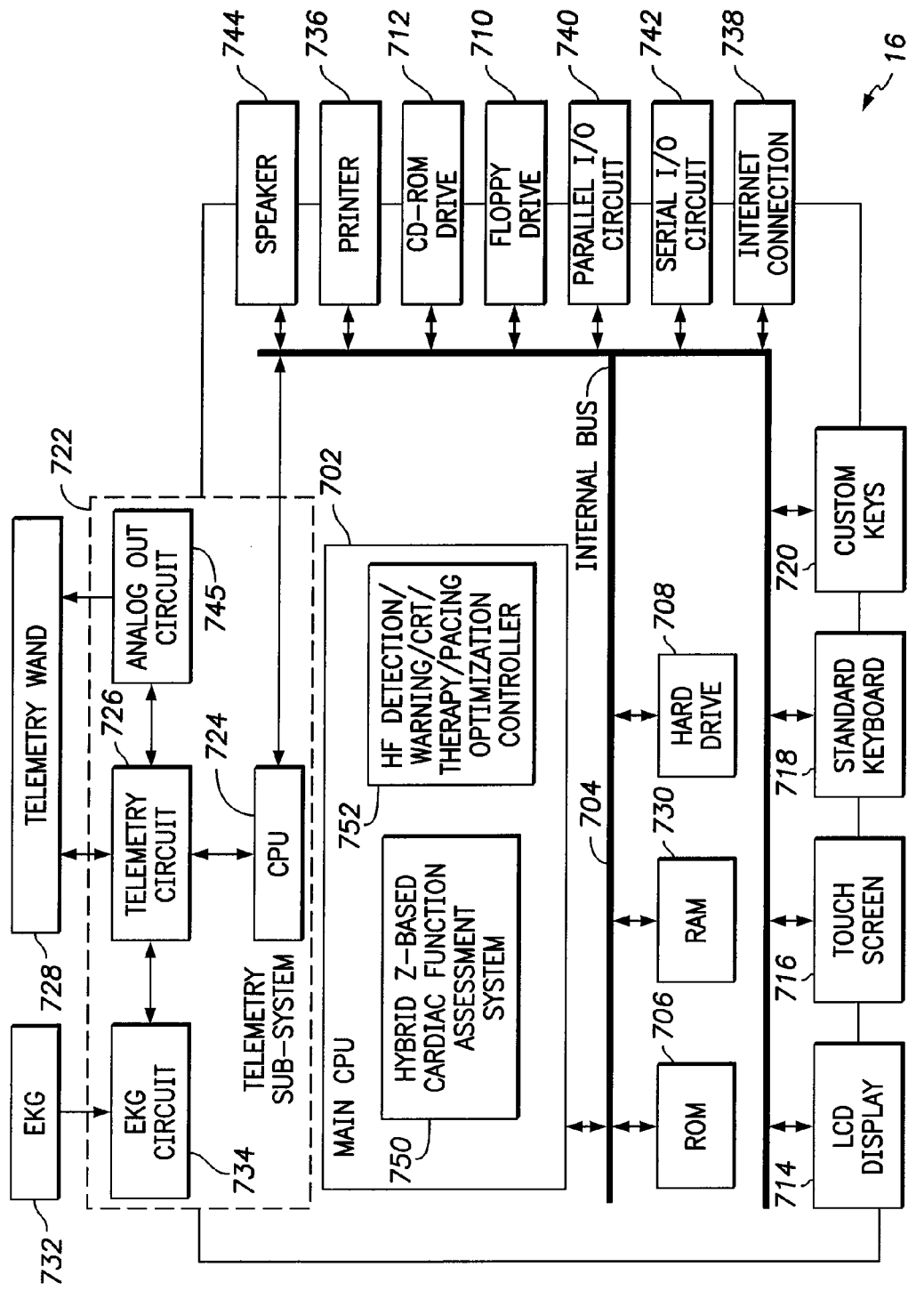
FIG. 14 is a functional block diagram illustrating components of the external device programmer of FIG. 1 and particularly illustrating programmer-based optimization components for controlling the various stroke volume estimation techniques.

FIG. 14 illustrates pertinent components of an external programmer 16 for use in programming the device of FIG. 13 and for performing or controlling the above-described optimization techniques. For the sake of completeness, other device programming functions are also described herein. Generally, the programmer permits a physician, clinician or other user to program the operation of the implanted device and to retrieve and display information received from the implanted device such as intracardiac electrogram (IEGM) data and device diagnostic data. Additionally, the external programmer can be optionally equipped to receive and display electrocardiogram (ECG) data from separate external surface ECG leads that may be attached to the patient. Depending upon the specific programming of the external programmer, programmer 16 may also be capable of processing and analyzing data received from the implanted device and from the ECG leads to, for example, render preliminary diagnosis as to medical conditions of the patient or to the operations of the implanted device.

Now, considering the components of programmer 16, operations of the programmer are controlled by a CPU 702, which may be a generally programmable microprocessor or microcontroller or may be a dedicated processing device such as an ASIC or the like. Software instructions to be performed by the CPU are accessed via an internal bus 704 from a read only memory (ROM) 706 and random access memory 730. Additional software may be accessed from a hard drive 708, floppy drive 710, and CD ROM drive 712, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 714 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 716 overlaid on the LCD display or through a standard keyboard 718 supplemented by additional custom keys 720, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 16 to retrieve data stored within any implanted devices and to also retrieve ECG data from ECG leads, if any, coupled to the patient. To this end, CPU 702 transmits appropriate signals to a telemetry subsystem 722, which provides components for directly interfacing with the implanted devices, and the ECG leads. Telemetry subsystem 722 includes its own separate CPU 724 for coordinating the operations of the telemetry subsystem. Main CPU 702 of programmer communicates with telemetry subsystem CPU 724 via internal bus 704. Telemetry subsystem additionally includes a telemetry circuit 726 connected to telemetry wand 728, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an ECG circuit 734 for receiving surface ECG signals from a surface ECG system 732. In other implementations, the ECG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the device also includes the data stored within the recalibration database of the device (assuming the device is equipped to store that data.) Data retrieved from the implanted devices is stored by external programmer 16 either within a random access memory (RAM) 730, hard drive 708 or within a floppy diskette placed within floppy drive 710. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 16, the implanted devices may be further controlled to transmit additional data in real time as it is detected by the implanted devices, such as additional IEGM data, lead impedance data, and the like. Additionally, or in the alternative, telemetry subsystem 722 receives ECG signals from ECG leads 732 via an ECG processing circuit 734. As with data retrieved from the implanted device itself, signals received from the ECG leads are stored within one or more of the storage devices of the external programmer. Typically, ECG leads output analog electrical signals representative of the ECG. Accordingly, ECG circuit 734 includes analog to digital conversion circuitry for converting the signals to digital data appropriate for further processing within the programmer. Depending upon the implementation, the ECG circuit may be configured to convert the analog signals into event record data for ease of processing along with the event record data retrieved from the implanted device. Typically, signals received from the ECG leads are received and processed in real time.

Thus, the programmer receives data both from the implanted devices and from optional external ECG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 702, the programming commands are converted to specific programmable parameters for transmission to the implanted devices via telemetry wand 728 to thereby reprogram the implanted devices. Prior to reprogramming specific parameters, the physician may control the external programmer to display any or all of the data retrieved from the implanted devices or from the ECG leads, including displays of ECGs, IEGMs, and statistical patient information. Any or all of the information displayed by programmer may also be printed using a printer 736.

Additionally, CPU 702 also includes a programmer-based hybrid Z-based cardiac function assessment system 750 operative to perform all or some of the functions of corresponding on-board system 601, discussed above, based on data transmitted to/from the implanted device, particularly the aforementioned stroke volume assessment functions. The microcontroller also includes a programmed-based HF detection/warning/CRT/therapy/pacing optimization controller 752 operative to perform or control all or some of the functions described above in response to the estimate of stroke volume, such as detecting and tracking HF, generating warnings, controlling CRT, optimizing pacing delay parameters, etc.

Depending upon the implementation, the various components of the CPU may be implemented as separate software modules or the modules may be combined to permit a single module to perform multiple functions. In addition, although shown as being components of the CPU, some or all of these components may be implemented separately using ASICs or the like.

Programmer/monitor 16 also includes an internet connection 738 to permit direct transmission of data to other programmers via the public switched telephone network (PSTN) or other interconnection line, such as a T1 line or fiber optic cable or wireless connection (WiFi). Depending upon the implementation, the internet connection may be connected directly to internal bus 704 may be connected to the internal bus via either a parallel port 740 or a serial port 742. Other peripheral devices may be connected to the external programmer via parallel port 740 or a serial port 742 as well. Although one of each is shown, a plurality of input output (I/O) ports might be provided, including USB ports, etc. A speaker 744 is included for providing audible tones to the user, such as a warning beep in the event improper input is provided by the physician. Telemetry subsystem 722 additionally includes an analog output circuit 745 for controlling the transmission of analog output signals, such as IEGM signals output to an ECG machine or chart recorder.

With the programmer configured as shown, a clinician or other user operating the external programmer is capable of retrieving, processing and displaying a wide range of information received from the implanted device and to reprogram the implanted device if needed. The descriptions provided herein with respect to FIG. 14 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for implant within a patient having a lead system including a right ventricular (RV) lead and a multi-pole left ventricular (LV) lead, the method comprising:
   injecting current between a reference electrode and an electrode in the RV lead;
   measuring values representative of impedance along different sensing vectors between the reference electrode and each of a plurality of sensing electrodes of the multi-pole LV lead, wherein the values representative of impedance are obtained using measurements of an electric field caused by the injected current; and
   estimating a parameter representative of stroke volume within the patient from a combination of the values representative of impedance.

2. The method of claim 1 wherein the reference electrode used to inject current is a relatively large electrode compared to the sensing electrodes of the LV lead.

3. The method of claim 1 wherein the reference electrode is a superior vena cava (SVC) coil electrode.

4. The method of claim 1 wherein the plurality of sensing electrodes of the LV lead include a tip electrode and a set of ring electrodes.

5. The method of claim 4 wherein the multi-pole LV lead is quad-pole lead comprising the tip electrode and three ring electrodes.

6. The method of claim 1 wherein the electrode in the RV lead used to inject current is an RV ring electrode.

7. The method of claim 1 wherein measuring values representative of impedance includes, for each electrode "i" of the LV lead, performing the steps of:
measuring impedance ($Z_i$) values between the electrode and the reference electrode over at least one heart beat while the current is being injected;
determining maximum and minimum impedance values (max $Z_i$ and min $Z_i$) with each heartbeat; and
determining a set of difference values ($\Delta Z_i$) based on the maximum and minimum impedance values (max $Z_i$ and min $Z_i$).

8. The method of claim 7 further including combining the impedance values to yield a combined impedance value by summing the set of difference values ($\Delta Z_i$) to yield a combined difference value ($\Delta Z_{sum}$).

9. The method of claim 8 wherein estimating the parameter representative of stroke volume includes estimating stroke volume.

10. The method of claim 9 wherein stroke volume is estimated from the combined difference value ($\Delta Z_{sum}$).

11. The method of claim 1 further including detecting a heart failure parameter based on the parameter representative of stroke volume.

12. The method of claim 1 further including tracking heart failure based on the parameter representative of stroke volume.

13. The method of claim 1 further including setting pacing delays based, at least in part, on the parameter representative of stroke volume.

14. The method of claim 13 wherein the parameter representative of stroke volume is stroke volume and wherein the pacing delays are set values sufficient to increase stroke volume within the patient.

15. The method of claim 13 wherein the parameter representative of stroke volume is cardiac output and wherein pacing delays are set values sufficient to increase cardiac output within the patient.

16. The method of claim 1 wherein all of the steps are performed by the implantable medical device.

17. The method of claim 1 wherein at least some of the steps are performed by an external device based on signals received from the implantable medical device.

18. The method of claim 1 wherein the values representative of impedance include one or more of impedance, admittance, conductance and immittance.

19. A system for use with an implantable medical device for implant within a patient having a lead system including a right ventricular (RV) lead and a multi-pole left ventricular (LV) lead, the system comprising:
a current injection system operative to inject current between a reference electrode and a ring electrode in the RV lead, wherein the reference electrode is a superior vena cava (SVC) coil electrode;
an impedance measuring system operative to measure values representative of impedance along different sensing vectors between the reference electrode and electrodes of the multi-pole LV lead, wherein the electrodes of the LV lead include a tip electrode and a set of ring electrodes, wherein the values representative of impedance are obtained using measurements of an electric field caused by the injected current; and
a stroke volume parameter estimation system operative to estimate parameters representative of stroke volume within the patient from a combination of the values representative of impedance.

20. A system for use with an implantable medical device for implant within a patient having a lead system including a right ventricular (RV) lead and a multi-pole left ventricular (LV) lead, the system comprising:
means for injecting current between a reference electrode and a ring electrode in the RV lead, wherein the reference electrode is a superior vena cava (SVC) coil electrode;
means for measuring values representative of impedance along different sensing vectors between the reference electrode and electrodes of the multi-pole LV lead, wherein the electrodes of the LV lead include a tip electrode and a set of ring electrodes, wherein the values representative of impedance are obtained using measurements of an electric field caused by the injected current; and
means for estimating a parameter representative of stroke volume within the patient from a combination of the values representative of impedance.

* * * * *